US007499584B2

(12) United States Patent
Delaney

(10) Patent No.: US 7,499,584 B2
(45) Date of Patent: Mar. 3, 2009

(54) SMEAR-LIMIT BASED SYSTEM AND METHOD FOR CONTROLLING VISION SYSTEMS FOR CONSISTENTLY ACCURATE AND HIGH-SPEED INSPECTION

(75) Inventor: Mark L. Delaney, Shoreline, WA (US)

(73) Assignee: Mitutoyo Corporation, Kawasaki-shi (JP)

( * ) Notice: Subject to any disclaimer, the term of this patent is extended or adjusted under 35 U.S.C. 154(b) by 916 days.

(21) Appl. No.: 10/971,504

(22) Filed: Oct. 21, 2004

(65) Prior Publication Data

US 2006/0088201 A1 Apr. 27, 2006

(51) Int. Cl.
  *G06K 9/00* (2006.01)
(52) U.S. Cl. .................. 382/152; 382/159
(58) Field of Classification Search .......... 382/141–152, 382/159; 348/92; 702/34–35
  See application file for complete search history.

(56) References Cited

U.S. PATENT DOCUMENTS

| | | | |
|---|---|---|---|
| 6,239,554 B1 | 5/2001 | Tessadro et al. | |
| 6,324,298 B1 | 11/2001 | O'Dell et al. | |
| 6,847,730 B1 * | 1/2005 | Beer et al. | 382/145 |
| 2003/0026457 A1 | 2/2003 | Nahum | |
| 2003/0039388 A1 | 2/2003 | Ulrich et al. | |
| 2003/0053679 A1 * | 3/2003 | Horn et al. | 382/152 |
| 2004/0146295 A1 | 7/2004 | Furman et al. | |
| 2004/0223053 A1 | 11/2004 | Gladnick et al. | |

OTHER PUBLICATIONS

"Vision System Features Non-Stop Measurement Mode," *ThomasNet Industrial News Room*, Jun. 25, 2004 <www.ThomasNet.com/fullstory/> [retrieved Jan. 24, 2006].

"New, Quick Vision Stream™ CNC Vision Systems Measure 'On-the-Fly' for 5× Faster Throughput," *ThomasNet Industrial News Room*, Jun. 23, 2004 <www.ThomasNet.com/fullstory/> [retrieved Jan. 24, 2006].

* cited by examiner

*Primary Examiner*—Daniel G Mariam
(74) *Attorney, Agent, or Firm*—Christensen O'Connor Johnson Kindness PLLC

(57) ABSTRACT

A machine vision inspection system and method for generating a workpiece image acquisition/inspection program, which can be shared by different machine vision systems having different hardware capabilities. Each system includes a movable stage for scanning and measuring selected workpiece features, and preferably includes strobe lighting to control the effective exposure time of the workpiece image. The program provides for the determination of various image acquisition parameters, such as the stage velocity, strobe light power, strobe exposure time, etc., based on a functional limit related to image smear. Thus, the program automatically adapts to any specific system, by allowing determination of optimal image acquisition parameters for that system based on the functional limit. Accordingly, the same program is usable on different systems to consistently provide a desired level of accuracy as well as optimum or near-optimum throughput, regardless of which vision system is used.

19 Claims, 6 Drawing Sheets

SMEAR-LIMIT BASED SYSTEM AND METHOD FOR CONTROLLING VISION SYSTEMS FOR CONSISTENTLY ACCURATE AND HIGH-SPEED INSPECTION

FIELD OF THE INVENTION

The invention relates generally to methods for programming and operating machine vision inspection systems having a camera and stage that are movable relative to one another in multiple directions so as to scan and inspect selected features of a workpiece on the stage. More particularly, it relates to systems and methods for creating a single computer script based on a functional limit related to image smear, such that the script operates reliably to achieve high levels of inspection accuracy and speed on a variety of machine vision inspection systems that have differing operating specifications.

BACKGROUND OF THE INVENTION

Precision machine vision inspection systems (or "vision systems" in short) can be utilized to obtain precise dimensional measurements of inspected objects and to inspect various other object characteristics. Such systems may include a computer, a camera and optical system, and a precision stage that is movable in multiple directions so as to allow the camera to scan the features of a workpiece that is being inspected. One exemplary prior art system that is commercially available is the QUICK VISION® series of PC-based vision systems and QVPAK® software available from Mitutoyo America Corporation (MAC), located in Aurora, Ill. The features and operation of the QUICK VISION® series of vision systems and the QVPAK® software are generally described, for example, in the QVPAK 3D CNC Vision Measuring Machine Users Guide, published January 2003, and the QVPAK 3D CNC Vision Measuring Machine Operation Guide, published September 1996, each of which is hereby incorporated herein by reference in their entirety. This product, as exemplified by the QV-302 Pro model, for example, is able to use a microscope-type optical system to provide images of a workpiece at various magnifications, and move the stage as necessary to traverse the workpiece surface beyond the limits of any single video image. A single video image typically encompasses only a portion of the workpiece being observed or inspected, given the desired magnification, measurement resolution, and physical size limitations of such systems.

Machine vision inspection systems generally utilize automated video inspection. U.S. Pat. No. 6,542,180 teaches various aspects of such automated video inspection and is incorporated herein by reference in its entirety. As taught in the '180 patent, automated video inspection metrology instruments generally have a programming capability that allows an automatic inspection event sequence to be defined by the user for each particular workpiece configuration. This can be implemented by text-based programming, for example, or through a recording mode which progressively "learns" the inspection event sequence by storing a sequence of machine control instructions corresponding to a sequence of inspection operations performed by a user, or through a combination of both methods. Such a recording mode is often referred to as "learn mode" or "training mode". Once the inspection event sequence is defined in "learn mode," such a sequence can then be used to automatically acquire (and additionally analyze or inspect) images of a workpiece during "run mode."

The machine control instructions, including the specific inspection event sequence including image acquisition parameters, etc., are generally stored as a "part program" or "workpiece program" that is specific to the particular workpiece configuration. The ability to create part programs with instructions that perform a predetermined sequence of inspection operations provides several benefits, including enhanced inspection repeatability, as well as the ability to automatically execute the same part program on a plurality of compatible machine vision inspection systems belonging to an industrial user and/or at a plurality of times.

For general-purpose machine vision inspection systems that are intended to be rapidly programmable for a wide variety of workpieces, as exemplified by the previously referenced QUICK VISION® series of PC-based vision systems, it has been conventional for image acquisition operations to be interspersed with image analysis operations and/or feature inspection operations that are performed on the most recently acquired image. However, there is an increasing demand for general-purpose machine vision inspection systems to provide higher throughput. According to one method, this may be accomplished by performing image acquisition while using continuous relative motion between the camera and the workpiece stage (as opposed to intermittently stopping and starting the relative motion, as required in the interspersing vision system), thereby significantly increasing inspection throughput. It is advantageous for such systems to include strobe lighting illumination to assist with the acquisition of images during continuous motion without smearing (or blurring) the image.

High-speed "in-line" vision inspection systems used in high-speed production lines have used strobe lighting illumination to minimize image smearing. However, such in-line vision systems typically are dedicated to a single production line and acquire the "same" image over and over again, for successive workpieces on a conveyor system, for example. In such cases, for each image the motion speed and strobe illumination parameters, etc., are the same. Furthermore, workpiece configurations are rarely changed. Thus, programming methods for such systems have not facilitated rapid programming for an unlimited variety of workpieces by relatively unskilled users, and have not been "transportable" between vision systems having different operating characteristics.

In contrast, experience has shown that it is essential for general-purpose machine vision inspection systems to facilitate rapid programming for an unlimited variety of workpieces by relatively unskilled users. Furthermore, in modern "flexible manufacturing" environments, for both machine scheduling flexibility and consistent quality control, it is desirable for the same part program to run on different vision systems without modification. Furthermore, it is essential that the inspection results generated from different vision systems provide comparable accuracy, so that the results can be compared, tallied, etc., to produce meaningful inspection and quality control data. Furthermore, it is desirable that each machine that runs a given part program achieves approximately the highest possible throughput, in a manner consistent with the objectives outlined above. However, different vision systems typically have different operating characteristics such as different maximum stage speeds, stage axis encoder resolutions, strobe lighting maximum power and/or minimum duration, etc., even among different versions or generations of the same model or class of machine. Therefore, the objectives outlined above have not been achieved, and a need exists for precision machine vision inspection systems and methods that create a part program that can be used with different vision systems having different operating characteristics, and that adapts to the operating characteristics of each system to consistently and reliably provide both a high level of inspection throughput, and inspection results that have a desired level of accuracy.

SUMMARY OF THE INVENTION

A machine vision inspection system and method is provided for creating a part program that is usable on different vision systems, and that consistently provides a desired level of accuracy as well as optimum or near-optimum throughput, regardless of which vision system is used.

A high-throughput precision machine vision inspection system may include strobe lighting illumination to assist with the acquisition of images during continuous motion. The strobe exposure time can be significantly shorter than an inherent minimum exposure time of a camera of the machine vision inspection system, thus "freezing" the workpiece with respect to the camera during image acquisition, and providing an image that is relatively smear-free (or blur-free) and well suited for supporting high-precision inspection. However, to provide a single part program that reliably provides smear free images on a variety of precise machine vision inspection and measurement systems with different operating characteristics requires a novel machine vision inspection system programming method that takes several factors into consideration with adequate precision. For example, the maximum motion speed that may be used without excessive image smear is generally limited by the maximum power level and/or minimum exposure time of the strobe lighting system. Accordingly, for a given motion speed, if two vision systems have different minimum strobe exposure times, and if the part program specifies that a vision system uses its own minimum strobe exposure time, then the resulting image from the vision system with a relatively longer strobe exposure time will have more smear than the image from the vision system with a relatively shorter strobe exposure time. Thus, the resulting images and inspection results will not be reliably controlled or comparable. A relatively poor solution to this problem is for the part program to specify a strobe exposure time and/or related motion speed that falls within the operating characteristics of any vision system that might be used. However, this approach does not take advantage of the shorter minimum strobe exposure time and higher motion speed available with relatively high-capability vision systems, and will thus "arbitrarily" limit their potential throughput.

This invention provides systems and methods for the strobe power level, strobe exposure time, and motion speed for an inspection image to be chosen in combination to provide sufficient illumination and reduce motion smear (blur) so as to provide workpiece images that support inspection and measurement results well within the related inspection feature tolerances of the workpiece, even when continuous motion is used during image acquisition. Various considerations related to the operation of a high-throughput vision system, and related to determining operable combinations of strobe power level, strobe exposure time, and motion speed, are described in co-assigned, co-pending U.S. patent application Ser. Nos. 10/435,625, and 10/719,210 which are hereby incorporated herein by reference.

In various exemplary embodiments, a first (initial) precision machine vision inspection system is programmed to inspect a workpiece. The precision machine vision inspection system includes an image acquisition system having at least a camera; at least one light source (e.g., strobe light) having a maximum light power; a workpiece stage; and a control system portion. At least one of the workpiece stage and the camera is movable to provide relative motion having a maximum velocity with respect to each other. The camera and/or light source defines a minimum effective exposure time. The programming method generally includes five steps.

In step 1, a functional limit related to image smear is determined for the program. One example of such a functional limit is a "smear limit," which is the amount of relative motion allowed between the camera and the workpiece during the effective image exposure time (e.g., strobe exposure time). The lesser the smear limit (i.e., the less the amount of relative motion that is allowed during exposure time), the less image smear, and hence the greater accuracy in inspection results. However, for a given strobe intensity and duration, the lesser the smear limit the slower the allowable relative motion speed between the camera and the workpiece, and hence the lesser inspection throughput.

In view of the dependence of inspection accuracy on the amount of image smear, and the tradeoff between image smear and speed (or throughput), according to the present invention, in various embodiments a smear limit is used to determine various image acquisition parameters (e.g., light power level, exposure time, relative motion speed, etc.) to achieve a desired level of accuracy, at the highest possible speed that is consistent with the desired level of accuracy. In other words, the priority is placed on ensuring the desired level of accuracy, perhaps, at the expense of the highest possible speed, which may need to be set lower than the potential maximum speed allowed by the hardware capabilities of each vision system.

In step 2, an optimal exposure time is determined for the program. The optimal exposure time may be determined in conjunction with a selected or predetermined light power level. Typically, the light power level is set as the maximum light power level possible with the particular light source used, so that the exposure time can be minimized and the motion speed maximized for a particular image. The optimal exposure time for a particular image at the selected light power level may be determined to achieve a desired image characteristic manually, semi-automatically, or automatically (e.g., by utilizing any known or later developed video tool for achieving a desired image characteristic, such as an illumination level, contrast, or the like). In some exemplary embodiments, the optimal exposure time is defined so as to achieve a desired gray level, edge contrast, etc., in an acquired image. When the "optimal" exposure time is determined manually, it may simply correspond to an acceptable image in the judgment of a machine operator or programmer. An "optimal" exposure time need not be mathematically optimized as the term is used herein. Rather, for a given workpiece feature, an "optimal" exposure time is generally relatively faster on a relatively higher-performance machine having the capability to make it faster, and slower on a relatively lower-performance machine that limits it to being slower.

In step 3, an operational relative velocity between the workpiece and the workpiece stage is determined based on the smear limit, and the optimal exposure time determined in step 2 above. In various exemplary embodiments, the determination of the operational relative velocity includes generally four sub-steps. First, a relative velocity is calculated based on the smear limit and the optimal exposure time. (Relative Velocity=Smear Limit/Optimal Exposure Time.) Second, the calculated relative velocity is compared with the maximum relative motion velocity of the current vision system to determine which one has a lower value. Third, if the calculated relative velocity is lower, then the calculated relative velocity is set as the operational relative velocity. Fourth, on the other hand, if the maximum relative motion velocity of the current vision system is lower, then the maximum relative motion velocity is set as the operational relative velocity.

In step 4, the total exposure energy may be calculated based on the operational exposure time and the selected light power level. (Total Exposure Energy=Operational Exposure Time× Selected Light Power Level.) Alternatively, operations which determine and/or set an exposure time may simultaneously effectively define one or more parameters that correspond to, or inherently identify, the total exposure energy without "calculation". For example, for machine visions systems that can operate with a strobe light source using a constant predetermined light source power level, such machine vision systems may include a scale of respective numerical illumination settings that correspond to particular respective light strobe durations. Thus, each respective numerical illumination setting corresponds to or inherently identifies the total exposure energy. In either case, essentially, the total exposure energy is correlated to the number of photons incident on a particular feature of the workpiece being imaged during the operational exposure time.

In step 5, the functional limit (e.g., smear limit) and the total exposure energy (or a parameter indicative of the total exposure energy) are stored as part of a part program (or a workpiece program), which defines a sequence of image acquisition and inspection operations for the workpiece. As previously noted, when a machine vision system can operate with a strobe light source that uses a constant predetermined light source power level, a respective illumination setting that corresponds to a particular respective light strobe duration, that is, a particular exposure time, provides a parameter indicative of the total exposure energy.

The steps described above may be performed during "learn mode" or "training mode" of the current vision system. It should be noted that, in many applications, the method may be at least partially repeated for each of a set of images used to inspect the entire workpiece. The resulting part program, including set(s) of the functional limit and the total exposure energy parameters for acquiring inspection image(s) of the workpiece at a user-specified accuracy level with respect to the current vision system, may then be passed onto and run on a different vision system in "run mode". During run mode, the different vision system determines system-specific image acquisition parameters based on its system-specific operating characteristics or limitations and the functional limit and the total exposure energy parameters included in the part program, to produce workpiece images that support inspection results at the same or greater level of accuracy.

Specifically, the part program generated according to the methods and systems of the present invention in various exemplary embodiments can be automatically adapted to any specific vision system, based on the functional limit and the total exposure energy. In particular, the automatic adaptation process includes calculating various image acquisition operation parameters for the new vision system, based on the functional limit and the total exposure that have been passed on from the part program determined on the first (initial) vision system, to achieve the same or greater level of inspection accuracy, with high throughput, on the new vision system. The automatic adaptation of the part program provides nominally the same results in terms of the functional limit and total exposure energy and occurs on-the-fly, at least partially for each of a set of images used to inspect the entire workpiece, at the beginning of "run mode" of the new vision system. The automatic adaptation involves generally four steps.

In step 1, operating characteristics including the maximum light power, maximum relative motion velocity, and minimum effective exposure time of the new vision system, on which the part program is run, are identified.

In step 2, the smear limit and the total exposure energy (or a parameter indicative of the total exposure energy), together with any motion instructions controlling the workpiece inspection event sequence, are received from the part program.

In step 3, an optimal exposure time for the new vision system is calculated or otherwise determined based on the total exposure energy (or a parameter indicative of the total exposure energy) and a selected or predetermined light power level. In one exemplary embodiment, the calculation of the optimal exposure time involves generally four sub-steps. First, an exposure time is calculated or determined based on the total exposure energy and the selected light power level, for example the maximum light power level of the new system. (For example, Exposure Time=Total Exposure Energy/Selected Light Power Level.) Alternatively, a parameter indicative of the total exposure energy may correspond to an exposure time used with a constant predetermined light source power level, and may inherently indicate the optimal exposure time for appropriately calibrated systems.) Second, the calculated or determined exposure time is compared with the minimum exposure time of the new system to determine which one has a longer value. Third, if the calculated exposure time is longer, then the calculated exposure time is set as the optimal exposure time. Fourth, if the minimum exposure time is longer, then the minimum exposure time is set as the optimal exposure time, and further, the light power level is recalculated based on the total exposure energy and the minimum exposure time. (Recalculated Light Power Level=Total Exposure Energy/Minimum Exposure Time).

In step 4, an operational relative velocity is calculated based on the smear limit and the optimal exposure time. In various exemplary embodiments, the calculation of the operational relative velocity for the new vision system involves generally four sub-steps. First, a relative velocity is calculated based on the smear limit and the optimal exposure time. (Relative Velocity=Smear Limit/Optimal Exposure Time.) Second, the calculated relative velocity is compared with the maximum relative motion velocity of the new system to determine which one has a lower value. Third, if the calculated relative velocity is lower, then the calculated relative velocity is set as the operational relative velocity. Fourth, on the other hand, if the maximum relative velocity of the new system is lower, then the maximum relative velocity is set as the operational relative velocity.

In various exemplary embodiments, the method of encoding a part program on a first (initial) vision system, which can then automatically adapt to a different vision system having different hardware capabilities, is embodied in a computer-readable medium comprising computer-executable instructions that generally automatically perform the method when loaded to a control system portion of a vision system.

In various exemplary embodiments, the method includes using continuous relative motion between the camera and the workpiece stage during image acquisition operations to increase inspection throughput. In various exemplary embodiments, one or more light sources of the machine vision inspection system include a light source strobing capability.

In summary, the present invention provides for a part program, which is highly portable and can run on various vision systems having different hardware capabilities, and that consistently provides a desired level of accuracy as well as optimum or near-optimum throughput, regardless of which vision system is used.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
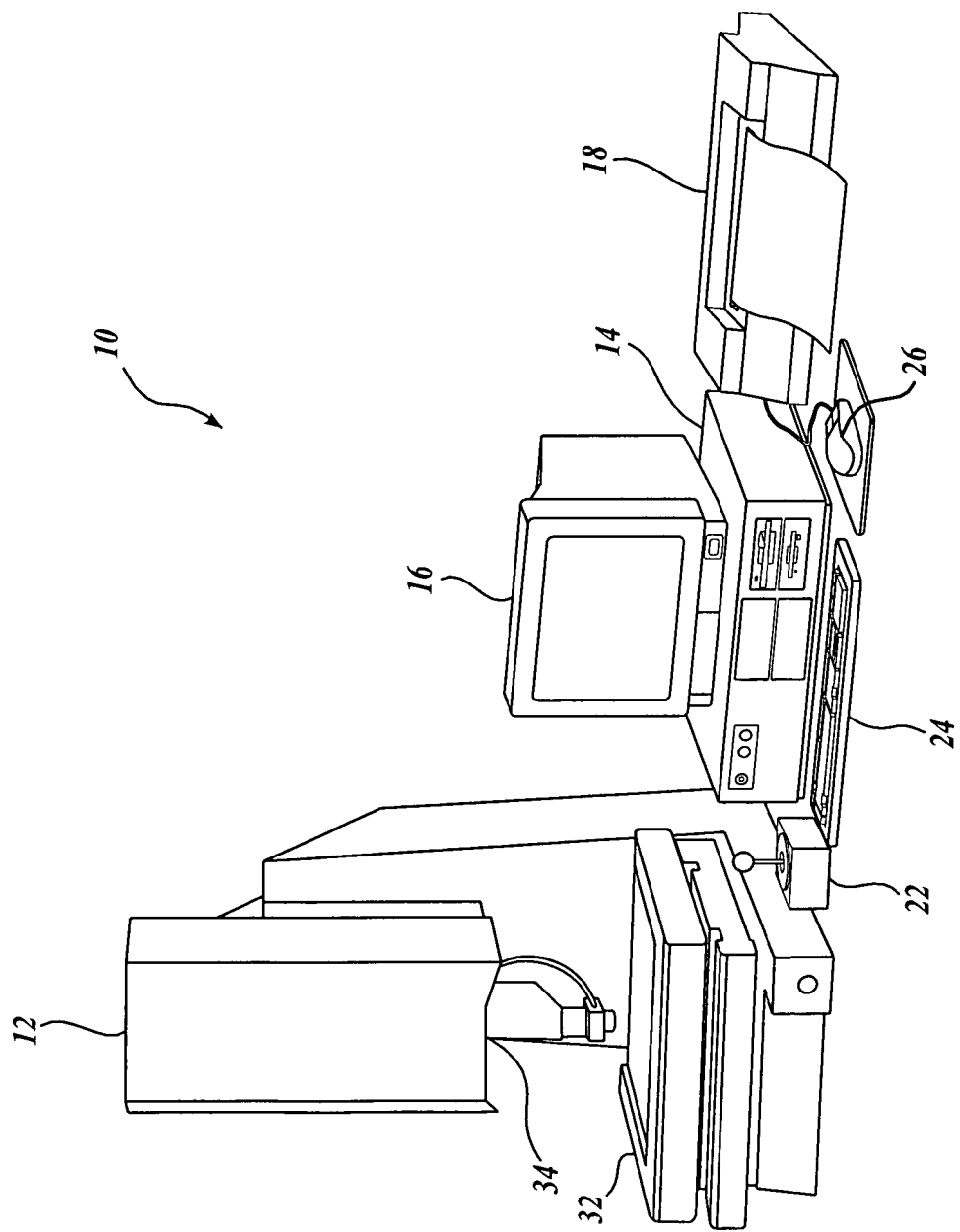
FIG. 1 is a diagram of a machine vision inspection system.

FIG. 1 is a block diagram of one exemplary machine vision inspection system 10 in accordance with the present invention. The machine vision inspection system 10 includes a vision measuring machine 12 that is operably connected to exchange data and control signals with a controlling computer system 14. The controlling computer system 14 is further operably connected to exchange data and control signals with a monitor 16, a printer 18, a joystick 22, a keyboard 24, and a mouse 26. The vision measuring machine 12 includes a moveable workpiece stage 32 and an optical imaging system 34 which may include a zoom lens or interchangeable lenses. The zoom lens or interchangeable lenses generally provide various magnifications for the images provided by the optical imaging system 34.

The joystick 22 can typically be used to control the movement of the movable workpiece stage 32 in both X and Y directions, which are generally parallel to the focal plane of the optical imaging system 34. The joystick 22 can also control the movement of the movable optical imaging system 34 in the Z or focus direction. Frequently, the Z axis movement is controlled by a rotary deflection component of a handle or knob of the joystick 22. The joystick 22 may be provided in a form other than that shown, such as any visual representation or widget on the monitor 16 which is intended to function as a "virtual motion control device" of the machine vision inspection system 10 and is controllable through any computer input device such as the mouse 26 or the like.

Figure 2:
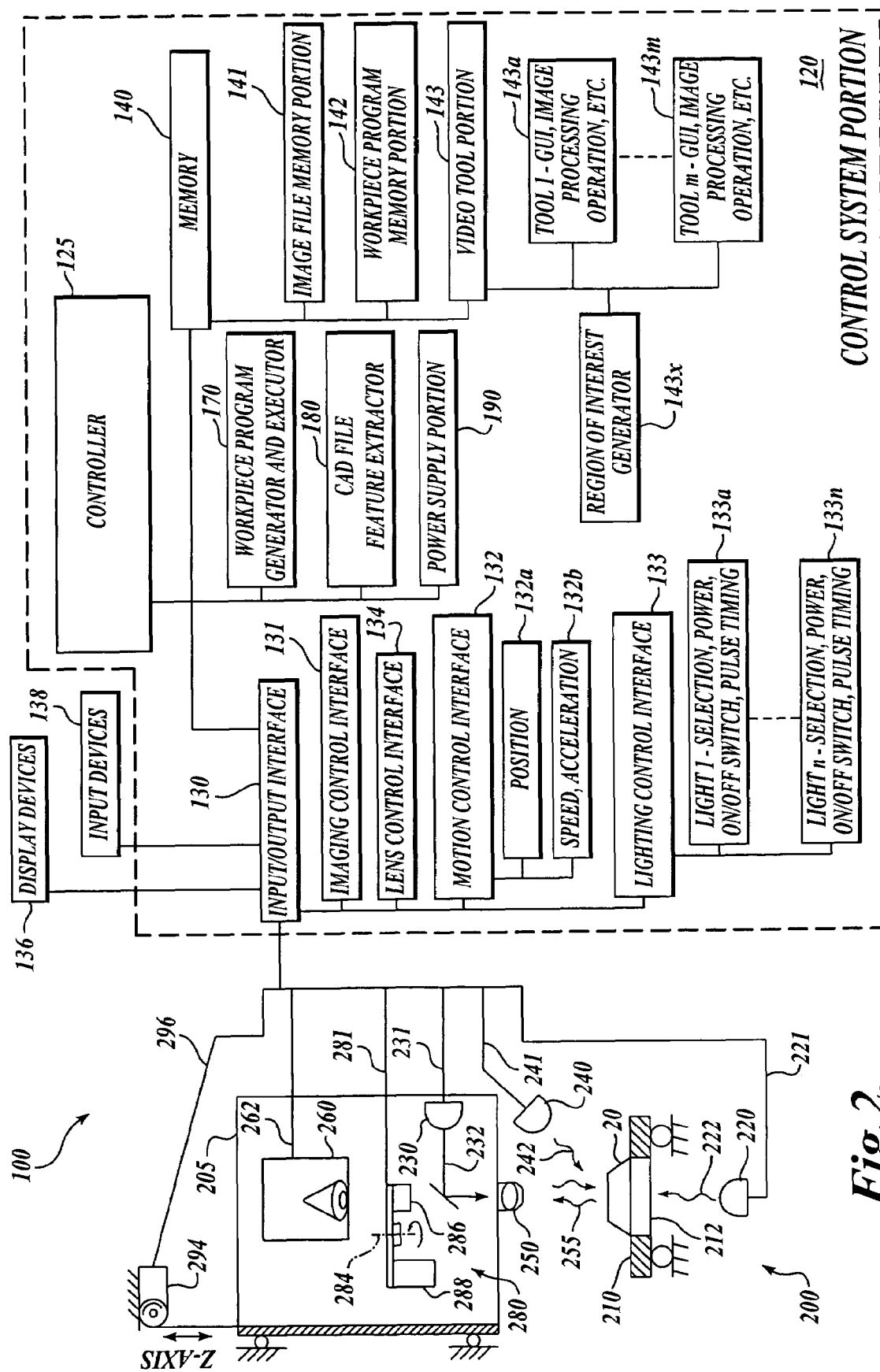
FIG. 2 is a diagram of a control system portion and a vision components portion of a machine vision inspection system.

FIG. 2 is a diagram of a control system portion 120 and a vision components portion 200 of a machine vision inspection system 100 in accordance with the present invention. As will be described in more detail below, the control system portion 120 is utilized to control the vision components portion 200. The vision components portion 200 includes an optical assembly portion 205, light sources 220, 230 and 240, and a workpiece stage 210 having a central transparent portion 212. The workpiece stage 210 is controllably movable along X and Y axes that lie in a plane that is generally parallel to the surface of the stage where a workpiece 20 may be positioned. The optical assembly portion 205 includes a camera system 260, an interchangeable objective lens 250, and may include a turret lens assembly 280, and the coaxial light source 230. Alternatively to the turret lens assembly, a fixed or manually interchangeable magnification-altering lens, or a zoom lens configuration, or the like, may be included. The optical assembly portion 205 is controllably movable along a Z axis that is generally orthogonal to the X and Y axes, by using a controllable motor 294, as described further below.

A workpiece 20 that is to be imaged using the machine vision inspection system 100 is placed on the workpiece stage 210. One or more of the light sources 220, 230 and 240 emits source light 222, 232, or 242, respectively, that is usable to illuminate the workpiece 20. Light emitted by the light sources 220, 230 and/or 240 illuminates the workpiece 20 and is reflected or transmitted as workpiece light 255, which passes through the interchangeable objective lens 250 and the turret lens assembly 280 and is gathered by the camera system 260. The image of the workpiece 20, captured by the camera system 260, is output on a signal line 262 to the control system portion 120.

The light sources 220, 230, and 240 that are used to illuminate the workpiece 20 can include a stage light 220, a coaxial light 230, and a surface light 240, such as a ring light or a programmable ring light, all connected to the control system portion 120 through signal lines or busses 221, 231 and 241, respectively. As a primary optical assembly of the machine vision inspection system 100, the optical assembly portion 205 may include, in addition to the previously discussed components, other lenses, and other optical elements such as apertures, beamsplitters and the like, such as may be needed for providing coaxial illumination, or other desirable machine vision inspection system features. When it is included, as a secondary optical assembly of the machine vision inspection system 100, the turret lens assembly 280 includes at least a first turret lens position and lens 286 and a second turret lens position and lens 288. The control system portion 120 rotates the turret lens assembly 280 along axis 284, between at least the first and second turret lens positions, through a signal line or bus 281.

The distance between the workpiece stage 210 and the optical assembly portion 205 can be adjusted to change the focus of the image of the workpiece 20 captured by the camera system 260. In particular, in various exemplary embodiments, the optical assembly portion 205 is movable in the vertical Z axis direction relative to the workpiece stage 210 using a controllable motor 294 that drives an actuator, a connecting cable, or the like, to move the optical assembly portion 205 along the Z axis. The term Z axis, as used herein, refers to the axis that is intended to be used for focusing the image obtained by the optical assembly portion 205. The controllable motor 294, when used, is connected to the input/output interface 130 via a signal line 296.

As shown in FIG. 2, in various exemplary embodiments, the control system portion 120 includes a controller 125, an input/output interface 130, a memory 140, a workpiece program generator and executor 170, a CAD file feature extractor 180, and a power supply portion 190. It will be appreciated that each of these components, as well as the additional components described below, may be interconnected by one or more data/control buses and/or application programming interfaces, or by direct connections between the various elements.

The input/output interface 130 includes an imaging control interface 131, a motion control interface 132, a lighting control interface 133, and a lens control interface 134. The motion control interface 132 includes a position control element 132a, and a speed/acceleration control element 132b. However, it should be appreciated that in various exemplary embodiments, such elements may be merged and/or indistinguishable. The lighting control interface 133 includes light control elements 133a-133n which control, for example, the selection, power, on/off switch, and strobe pulse timing if applicable, for the various corresponding light sources of the machine vision inspection system 100, such as the light sources 220, 230, and 240.

The memory 140 includes an image file memory portion 141, a workpiece program memory portion 142 that may include one or more part programs, or the like, and a video tool portion 143. The video tool portion 143 includes tool portions 143a-143m, which determine the GUI, image processing operation, etc., for each of the corresponding tools. The video tool portion 143 also includes a region of interest generator 143x that supports automatic, semi-automatic and/or manual operations that define various regions of interest that are operable in various video tools included in the video tool portion 143. In general, the memory portion 140 stores data usable to operate the vision system components portion 200 to capture or acquire an image of the workpiece 20 such that the acquired image of the workpiece 20 has desired image characteristics. The memory portion 140 further stores data usable to operate the machine vision inspection system 100 to perform various inspection and measurement operations on the acquired images, either manually or automatically, and to output the results through the input/output interface 130. The memory portion 140 also contains data defining a graphical user interface operable through the input/output interface 130.

The signal lines or busses 221, 231 and 241 of the stage light 220, the coaxial light 230, and the surface light 240, respectively, are all connected to the input/output interface 130. The signal line 262 from the camera system 260 and the signal line 296 from the controllable motor 294 are connected to the input/output interface 130. In addition to carrying image data, the signal line 262 may carry a signal from the controller 125 that initiates image acquisition.

One or more display devices 136 and one or more input devices 138 can also be connected to the input/output interface 130. The display devices 136 and input devices 138 can be used to view, create and/or modify part programs, to view the images captured by the camera system 260, and/or to directly control the vision system components portion 200. In a fully automated system having a predefined part program (or workpiece program), the display devices 136 and/or the input devices 138 may be omitted.

With regard to the CAD file feature extractor 180, information such as a CAD file representing a workpiece, or a previous image of a substantially identical workpiece, is frequently available in industrial applications of machine vision inspection systems. In the case of a CAD file representation, it should be appreciated that the locations of edges and boundaries in the CAD file representation may be determined manually, in a semi-automated fashion, or fully automatically from a CAD representation, by a variety of known methods of CAD file feature extraction.

In various exemplary embodiments of the present invention, a part program generally consists of at least two types of instructions, which may be arranged as cooperating programs, subprograms or subroutines, or intermixed instructions: workpiece image acquisition instructions that control image acquisition, and workpiece image analysis/inspection instructions that control image analysis/inspection. The overall construction and operation of various programs for "high-throughput" operation of a machine vision inspection system are disclosed in detail with reference to FIGS. 4 and 5, respectively, of the '625 application incorporated above. In various exemplary embodiments, when a user utilizes the machine vision inspection system 100 to create a workpiece image acquisition program for the workpiece 20, the user generates workpiece program instructions either by explicitly coding the instructions automatically, semi-automatically, or manually, using a workpiece programming language, or by generating the instructions by moving the machine vision inspection system 100 through an image acquisition training sequence such that the workpiece program instructions capture the training sequence. This process is repeated for multiple images in a set of images that are to be captured. These instructions, when executed, will cause the machine vision inspection system to manipulate the workpiece stage 210 and/or the camera system 260 at certain speed(s) such that a particular portion of the workpiece 20 is within the field of view of the camera system 260 and at a desired focus state for each of a set of images to be acquired. In addition to the program instructions that control the relative movement of the camera and the workpiece, the workpiece image acquisition program also needs to include program instructions that activate one or more of the light sources 220-240 to provide a desired illumination of the workpiece 20 during each image acquisition. As will be more fully described below in reference to FIGS. 4 and 5, the present invention is generally directed to generating program instructions, including the instructions that control the relative motion speed and lighting during image acquisition, which can be used by multiple vision systems to provide maximized inspection throughput, subject to the constraint of consistently producing workpiece images that support inspection results having a desired level of accuracy.

Once a set of workpiece image acquisition instructions are defined, in various exemplary embodiments of the present invention, the control system 120 executes the instructions and commands the camera system 260 to capture one or more images of the workpiece 20 according to the instructions. The control system 120 will then, under control of the controller 125, input the captured image(s) through the input/output interface 130 and store the captured image(s) in the memory 140. The controller 125 may also display the captured images on the display device 136.

The control system portion 120 is further usable to recall captured and stored workpiece inspection images, to inspect and analyze workpiece features in such workpiece inspection images, and to store and/or output the inspection results. These methods are typically embodied in various video tools included in the video tool portion 143 of the memory 140. Such tools may include, for example, shape or pattern matching tools, edge and/or boundary detection tools, circle and dimension measuring tools, coordinate matching tools, and the like. For example, such tools are routinely used for the inspection of the positions of edges (or boundaries) on workpieces in a variety of commercially available machine vision inspection systems, such as the QUICK VISION® series of vision systems and the associated QVPAK® software that were discussed above.

Figure 3:
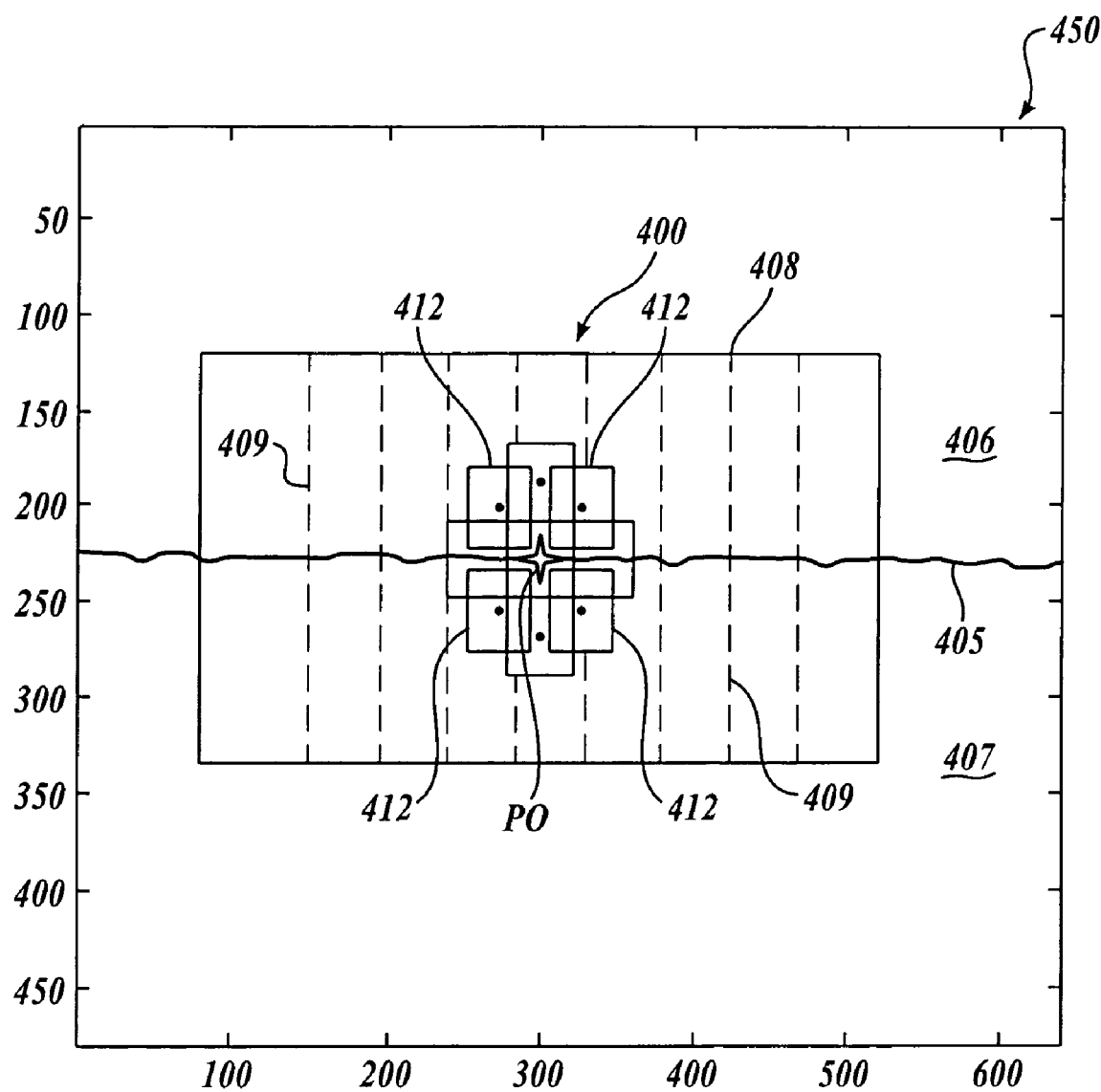
FIG. 3 is a diagram of one exemplary workpiece feature analysis/inspection tool usable in a machine vision inspection system to determine the location of an edge or boundary in a workpiece image.

FIG. 3 illustrates one example of such a video tool, i.e., a feature analysis/inspection tool that determines the location or position of an edge or boundary in a workpiece inspection image, disclosed in U.S. patent application Ser. No. 09/987,986, which is hereby incorporated herein by reference. The boundary tool 400 is usable to select an edge or boundary to be located. As shown in FIG. 3, a 640 by 480 pixel workpiece inspection image 450 includes a magnified image of a boundary 405 that extends horizontally across the image. The boundary 405 lies between two regions 406 and 407 that include different textures (not shown). In practice, a user can define an area-of-interest on the boundary 405, by using a graphical user interface to position the boundary tool 400 on a particular boundary portion to be detected, as shown in FIG. 3.

The area-of-interest is defined by the region of interest generator 143x based on the data corresponding to the positioned boundary tool 400. The boundary tool 400 includes a box 405 configurable by the user to further refine and determine the area-of-interest. For example, the box may be configured in an arc or circle shape, or in the shape of a rectangle as shown in FIG. 3. The boundary tool 400 may draw additional tool elements on the workpiece inspection image 450. For example, a point of interest P0 and region-of-interest indicators 412 shown as overlapping identical rectangles 412 (four rectangles 412 are shown in FIG. 3) may be automatically generated and drawn, and thereafter may be manually edited. The point of interest P0 may be only generally indicative of a point on the boundary 405. Moreover, the user can define a spacing between various "scan" lines 409 extending across the boundary in the area of interest, or the spacing can be automatically determined. Thus, operations associated with the boundary tool 400 can be manually defined by user input or by an automated process using predefined default characteristics for the boundary tool 400. By allowing the user to select a boundary tool 400 having predefined characteristics, boundary detection operations can be directed by operators having little or no understanding of the underlying mathematical or image processing operations.

The boundary tool 400 then performs a complex series of image analysis and/or image processing operations that compare various image characteristics in the various sets of opposing pairs of the regions of interest 412, to determine a set of image filtering characteristics, which most effectively indicate the location of the boundary 405 in the workpiece inspection image 450.

As outlined previously, in various exemplary embodiments, the machine vision inspection system 100 is used to create a workpiece image acquisition program consisting of workpiece program instructions. These instructions will control the movement of the workpiece stage 210 and/or the camera system 260 so as to capture a set of images of the workpiece 20, and also to activate one or more of the light sources 220-240 to provide a desired illumination of the workpiece 20 during image acquisition. Some exemplary methods of generating a workpiece image acquisition program (or a "motion path and image acquisition routine") and determining operable combinations of strobe power level, strobe exposure time, and motion speed, are described in the '625 and '210 applications incorporated above. The present invention is directed to improving "continuous motion" methods such as the methods described in the '625 and '210 applications by offering a "sub-method," which can be used to determine certain workpiece image acquisition parameters (e.g. the workpiece stage velocity, strobe power level, strobe exposure time, etc.) based on a functional limit related to image smear so that the resulting workpiece image acquisition program can be shared by a plurality of vision systems having different hardware operating characteristics or limitations. In one example, the method of the present invention generally improves or replaces various operations included in blocks 530 and/or 540 of the method shown in FIG. 4 of the '625 application.

Figure 4:
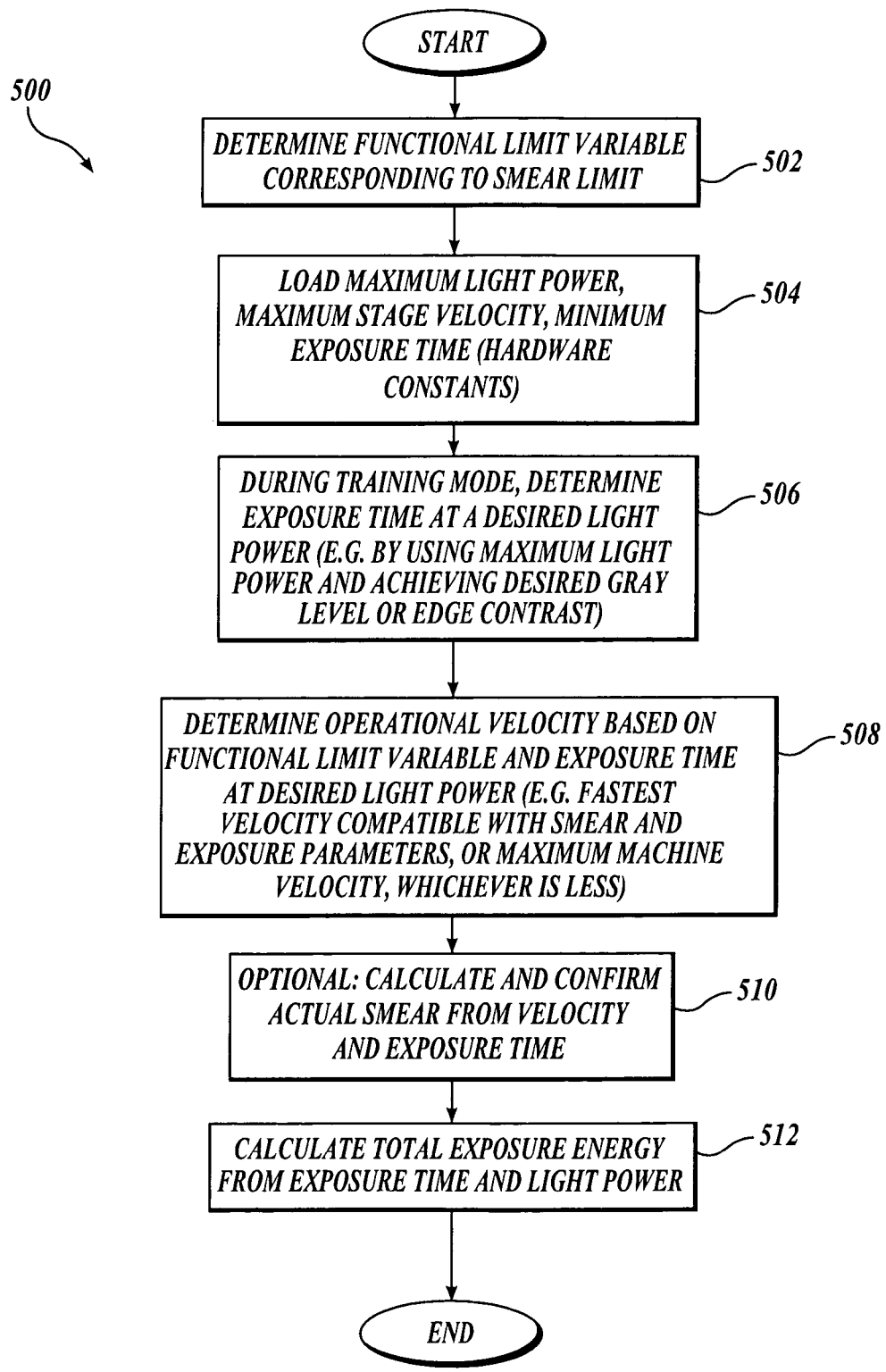
FIG. 4 is a flow diagram illustrating a method of determining a relative motion speed and various lighting control parameters based on a functional limit related to smear, to be carried out on a first (initial) vision system.

FIG. 4 is a flow diagram illustrative of one exemplary method (or routine) 500 for defining a relative motion speed and lighting control parameters (e.g., light power level, exposure time, etc.), in terms of a functional limit related to image smearing, for each of a set of images to be captured on the first (initial) vision system. The inventor has discovered that an efficient way to encode a continuous-motion workpiece image acquisition program, in a way such that the resulting program is highly portable amongst different vision systems while providing maximized inspection throughput in each different system, subject to the constraint of consistently producing workpiece images that support inspection results having a desired level of accuracy, is to specify a "smear limit," i.e., the amount of motion allowed between the camera and the workpiece (or the feature of the workpiece) during the strobe exposure time (i.e., the time during which strobe illumination occurs). For example, if a strobe lighting system has the strobe exposure time of 16.6 microseconds and the user specifies that the workpiece may move relative to the camera by no more than 0.25 microns during the exposure time, then 0.25 microns is the smear limit in this case. Consequently, the associated limit on the relative motion speed between the camera and the workpiece (e.g., the workpiece stage velocity) is calculated as 0.25 microns/16.6 microseconds, i.e., 15 mm per second. In this example, the smear limit has units of distance. The greater the smear limit, the more features will be smeared in the acquired image, and thus the ability to accurately locate an edge feature, or the like, will suffer, although the relative motion speed between the camera and the workpiece (and thus throughput) will increase. On the other hand, the lesser the smear limit (i.e., the smaller the amount of movement that is allowed between the workpiece and the camera during the strobe exposure time), the slower the allowable relative motion speed, and thus the inspection throughput will suffer, although the ability to accurately locate an edge feature, or the like, will increase. Accordingly, in any high throughput vision system, there is an inherent tradeoff between accuracy and speed (or throughput). In various exemplary embodiments, the methods of the present invention determine the relative motion speed and various lighting control parameters in the workpiece image acquisition instructions in terms of a functional limit related to smear (e.g., smear limit) in order to render the program highly portable among multiple vision systems, and also to strike an optimal, or near-optimal, balance between accuracy and speed for each vision system. In other words, the functional limit is used to determine various image acquisition parameters in the workpiece image acquisition instructions so that the program, when run on different vision systems, consistently produces inspection results having a desired level of accuracy, at the maximum speed that is consistent with the desired level of accuracy. Such an approach may require slower program execution to achieve the same level of accuracy when a program created on a higher-capability vision system is transferred to a lower-capability vision system. Slower program execution, however, is generally preferable over a loss of accuracy, because a loss of accuracy jeopardizes the validity of the inspection results and is hard to anticipate, detect, and characterize.

At a block 502, a functional limit variable (or a functional limit in short) or a smear limit variable related to a smear limit is determined in the routine 500. The functional limit variable or smear limit variable may be a smear limit in terms of distance, as outlined above, or may be any other variable(s) that are related to or indirectly indicative of the maximum allowable smear in a workpiece image that is used for inspection and measurement. For example, the functional limit variable may be a limit on the number of position encoder counts that correspond to displacement of the camera relative to the workpiece stage during the strobe exposure time. Such functional limits contribute to maintaining a specified overall machine measurement accuracy. As another example, the functional limit variable may be defined as an imaging tolerance, such as a percentage of a dimension of the field of view of the camera, or a displacement in terms of camera pixels, or the like. Such functional limits contribute to maintaining a desired level of subpixel interpolation accuracy when determining an edge feature location, or the like.

As another example, the functional limit variable may be defined as percentage of the dimensional tolerance of a feature to be inspected or measured in the image. For example, if a first feature is specified or intended to be at position $X_1$+/−20 microns, and a second feature is supposed to be at position $X_2$+/−5 microns, we could use this information to determine how much smear can be permitted without significantly jeopardizing the accuracy of measurement with respect to the required inspection accuracy. When such information is available from a CAD file, or by default settings, or otherwise by user input, we could set the smear limit to 10% (for example) of the specified feature tolerance, which would be 2 microns (or a corresponding number of encoder counts, or pixels, etc) for the first feature and 0.5 microns for the second feature. Such functional limits contribute to relaxing the functional limit to the maximum possible extent for each individual feature measurement, which tends to maximize the allowable motion speeds for each related workpiece image acquisition, thus maximizing inspection throughput while maintaining a desired level of accuracy for each individual measurement.

Therefore, while the following discussion mostly describes the present method as employing a smear limit as the functional limit variable, it should be understood that any other variable related to limiting smear in a workpiece image may be used as the functional limit variable. A smear limit or functional limit may be entered by the user, or may be automatically set according to a predefined default value, and/or may be calculated from various system characteristics (stage position measuring resolution, some fraction of the pixel spacing with or without consideration of a current magnification setting, or the like).

At a block 504, the maximum light power (e.g., the maximum strobe power), the maximum stage velocity, and the minimum (effective) exposure time (such as the minimum strobe duration time) of the current vision system are loaded to the routine 500. All of these three values are specified hardware operating characteristics of a specific vision system. In various embodiments according to the present invention, these operating characteristics are recorded in one or more memory portions of each specific vision system, for example as a machine configuration file or data, as a resource file or data, as plug-and-play component files or data, or the like, and may be retrieved under program control. The minimum exposure time of the vision system can be defined by either the camera or the illumination system (e.g., strobe lighting capability). For example, with continuous lighting, a camera having an electronic or mechanical shutter may be used to control the effective exposure. Generally, however, a strobe exposure time can be significantly shorter than an inherent minimum exposure time of a camera, and it would be difficult and/or costly to provide a physical or electronic shutter that can achieve a short exposure time comparable to the minimum exposure time of strobe lighting. Furthermore, the use of continuous lighting tends to generate excess heat, requiring an additional cooling system for the vision system. Therefore, in various exemplary embodiments of the present invention, strobe lighting, such as LED strobe lighting, is used to control the effective exposure of the vision system. Thus, the minimum exposure time of a vision system may be defined by the minimum strobe exposure time of the particular strobe lighting system used in a specific vision system.

At a block 506, during training mode (or learn mode) described above, for each of a set of images to be acquired, a suitable exposure time that is sufficiently long to achieve a desired edge contrast, the average image intensity or gray level, etc., at a desired light power, is determined for the current vision system. Typically, the light power is set at its maximum value because this will generally result in the shortest allowable strobe exposure time corresponding to a desired image intensity level, which in turn results in the least amount of smear for an inspection image taken at a given continuous motion speed. Therefore, in various exemplary embodiments of the present invention, the light power is set as the maximum light power setting of the light source included in the current vision system. The determination of the suitable exposure time may be performed manually, semi-automatically, or automatically in various exemplary embodiments. For example, to automatically determine the optimal exposure time that achieves a certain level of desirable edge (boundary) contrast, the desired light power may be set and the dual area contrast tool described in U.S. Pat. No. 6,542,180, which is incorporated herein by reference in its entirety, may be used in operations to identify a complementary strobe exposure time that provides an exposure level that provides a desired contrast difference across an edge, or that satisfies another desired image characteristic. Alternatively, the light setting methods described in U.S. Pat. No. 6,627,863, which is incorporated herein by reference in its entirety, may be used in operations to identify a complementary strobe exposure time that provides a desired image characteristic. As another example, the user may find the exposure time that achieves a desirable gray level by observation and adjustment of a displayed image, or by other experimental methods. A desirable gray level, edge contrast, etc., may be defined by the user, or may be predefined and automatically set by default. In any event, under ideal circumstances the optimal exposure time for achieving a desired edge contrast, gray level, etc., should be set as short as possible to minimize smear and also to increase the throughput (i.e., the shorter the exposure time that is used to image each feature of a workpiece, the faster the allowable motion, and therefore the faster the entire workpiece can be imaged).

At a block 508, an operational relative velocity between the camera and the workpiece is determined based on the previously determined smear limit and the previously determined optimal exposure time. In various exemplary embodiments, the determination of the operational relative velocity involves generally three steps. First, a relative velocity is calculated based on the smear limit and the exposure time. (Relative Velocity=Smear Limit/Optimal Exposure Time.) Second, the calculated relative velocity is compared with the maximum stage velocity of the current vision system loaded at block 504 above, to determine which one has a lower value. Third, if the calculated relative velocity is lower, then it is set as the operational relative velocity for the current vision system. On the other hand, if the maximum stage velocity is lower, the maximum stage velocity is set as the operational relative velocity for the current vision system. Optionally, in this case, the light power setting may be decreased, or the optimal exposure time increased, for example based on a ratio between the calculated relative velocity and the maximum stage velocity.

At a block 510, optionally, the operational relative velocity and the optimal exposure time determined for the current vision system can be used to calculate the actual operational value of the smear limit variable for the current vision system, to verify that it satisfies the maximum allowed value of the smear limit variable initially determined for the routine 500 at block 502 above. (Actual Smear Limit=Operational Relative Velocity×Optimal Exposure Time.) If the calculated actual smear limit deviates from the previously loaded smear limit by a predefined amount, an error may be reported to the user, or the routine 500 may automatically return to block 502 to specify a slightly different smear limit value to recalculate the operational relative velocity and optimal exposure time, for example.

At a block 512, the total exposure energy is calculated from the determined optimal exposure time and the known/desired light power level as selected at block 506 above. (Total Exposure Energy=Optimal Exposure Time×Known Light Power). The total exposure energy is correlated to the number of photons from the illumination source (e.g., strobe lighting) that strike the relevant portion or feature of the workpiece being imaged during the effective exposure time. The total exposure energy and the smear limit are then stored as part of the workpiece image acquisition program for the workpiece.

In various embodiments, blocks 506, 508, 510, and 512 will generally be repeated for each image of a set of inspection images to be acquired (i.e., for each of a set of features/portions on the workpiece to be inspected), particularly when the features of the workpiece to be inspected are dissimilar. In some embodiments, the same smear limit may be used for all of the images in the same set. In other embodiments, different smear limits may be used for different images for different features to be inspected within the set of images, for example based on individual feature tolerances, as outline above. In this case, block 502 will be additionally repeated for each of the set of images.

The sets of total exposure energy and smear limit(s), defined above for a set of images on the first (initial) vision system to achieve a desired gray level, edge contrast, etc. (i.e., desired inspection accuracy), form an operable set of machine-controlled instructions usable by various other vision systems to also acquire a set of workpiece inspection images that efficiently provide reliable inspection results. Specifically, the sets of total exposure energy and smear limit(s) can be used by different vision systems to determine a desirable set of operational relative velocities and lighting control parameter values specific to the respective vision systems, so as to consistently provide a set of inspection images that support a desired level of inspection accuracy, at a high speed consistent with the desired level of accuracy. As previously noted, the method described in reference to FIG. 4 above forms part of the overall method of generating an initial workpiece image acquisition program or part program. Thereafter, the sets of total exposure energy and smear limit (s) included in the program are passed on to different vision systems as part of the workpiece image acquisition program or part program that also includes various other instructions necessary for carrying out image acquisition and inspection, such as an inspection event sequence. More precisely, since a part program includes both workpiece image acquisition instructions and a workpiece image analysis/inspection instructions, in various exemplary embodiments of the present invention, the sets of total exposure energy and smear limit(s) are passed on as part of the part program that includes the workpiece image acquisition instructions, which in turn includes the sets of total exposure energy and smear limit(s).

Figure 5:
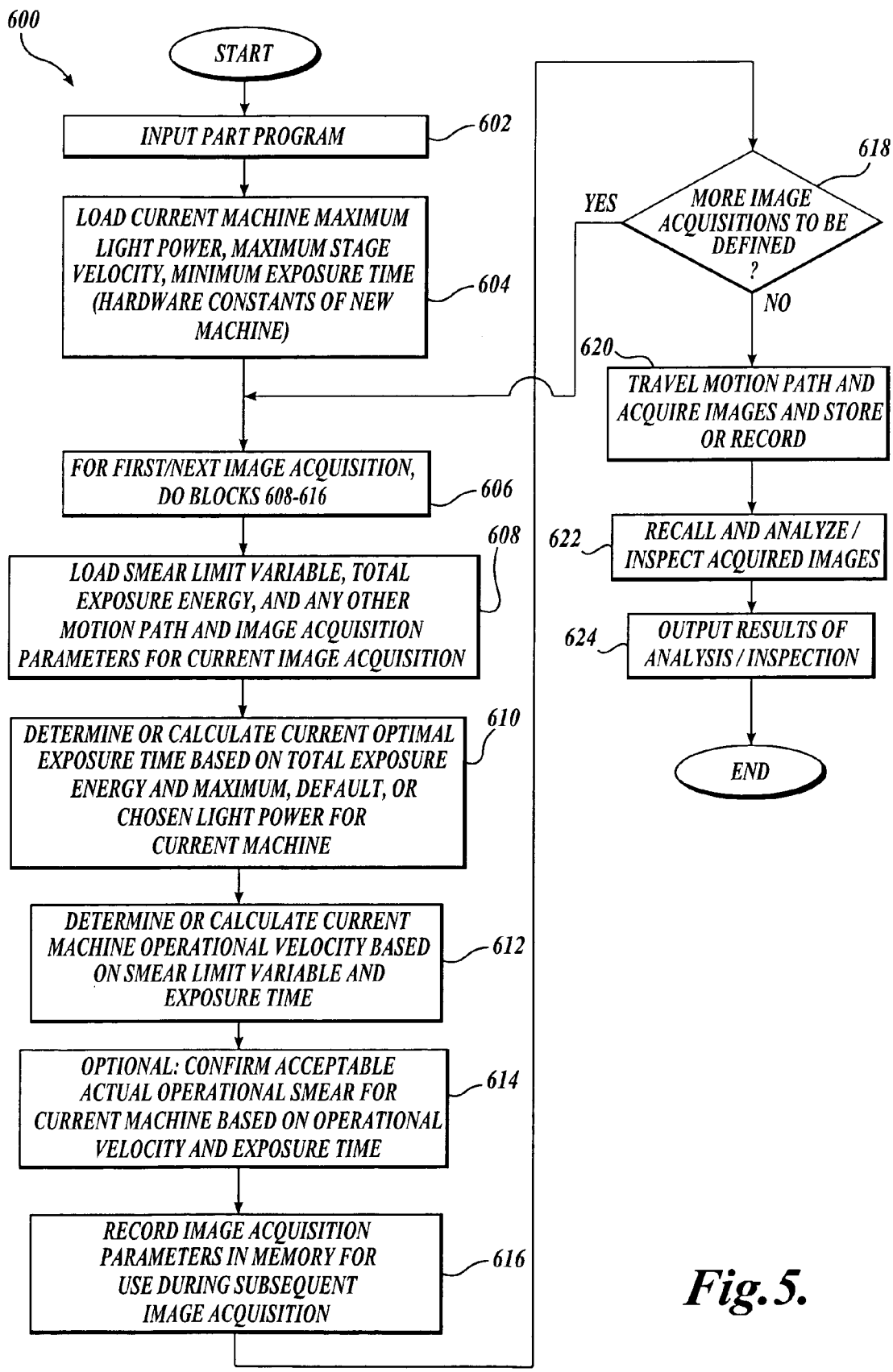
FIG. 5 is a flow diagram illustrating a method of determining a relative motion speed and various lighting control parameters for each of a set of images based on a functional limit and related parameters such as those determined according to the method shown in FIG. 4, followed by a further method of acquiring and inspecting/analyzing a set of images, to be carried out on each of any other (subsequent) vision systems.

FIG. 5 is a flow chart illustrative of one exemplary method or routine 600 to be carried out during "run mode" of the initial machine vision inspection system, or any other (or subsequent) vision system, which is different from the first (initial) vision system used to define the part program as discussed above. As will be more fully described below, the part program, or more specifically its workpiece image acquisition program instructions, defined on the first vision system, can automatically adapt to any given vision system. The automatic adaptation involves calculating optimal workpiece image acquisition parameters that are specific to the given vision system so as to maintain a desired level of inspection accuracy, while moving at the highest possible speed that is consistent with the required level of accuracy.

At a block 602, the routine 600 receives a previously defined part program including workpiece image acquisition instructions, which in turn include sets of total energy exposure and smear limit(s), as defined on the first vision system.

At a block 604, the current (new) vision system's maximum light power, maximum stage velocity, and minimum exposure time are loaded to the routine 600. As discussed in reference to block 504 of FIG. 4, all of these three variables are specified hardware operating characteristics of a specific vision system. In various embodiments according to the present invention, these operating characteristics are recorded in one or more memory portions of each specific vision system, for example as a machine configuration file or data, as a resource file or data, as plug-and-play component files or data, or the like, and may be retrieved under program control.

At a block 606, regarding the acquisition of the first or next image out of the set of inspection images to be acquired, it is commanded that the following blocks 608, 610, 612, 614, and 616 are to be performed.

At a block 608, the smear limit variable, total exposure energy and any other image acquisition commands or program instructions associated with acquiring the current image (such as motion path instructions, inspection operation instructions, etc.) are recalled or otherwise determined in the routine 600. These are all defined in the part program input at block 602 above.

At a block 610, based on the total exposure energy and a known light power level, the optimal exposure time for the current image acquisition on the current vision system is calculated or otherwise determined (for example, by using a look-up table, or the like). As outlined previously, in various exemplary embodiments, the light power level may be set at the maximum light power level because this will generally result in the shortest allowable strobe exposure time and the least amount of smear for an inspection image acquired at a given relative motion speed. Alternatively, the light power level may be set at a desired level by the user, or may be predefined and automatically set by default. In various exemplary embodiments, a calculation of the optimal exposure time involves generally three steps. First, an exposure time is calculated based on the total exposure energy and the known light power. (Exposure Time=Total Exposure Energy/Known Light Power Level.) Second, the calculated exposure time is compared with the current vision system's minimum exposure time loaded at block 604 above, to determine which one has a longer value. Third, if the calculated exposure time is longer, then it is set as the optimal exposure time for the current vision system. On the other hand, if the current vision system's minimum exposure time is longer (i.e., if the calculated exposure time cannot be practiced on the current vision system), then the current vision system's minimum exposure time is set as the optimal exposure time, and the light power is adjusted to provide the total exposure energy value loaded at block 608 above. (Recalculated Light Power=Total Exposure Energy/Minimum Exposure Time.)

At a block 612, the operational relative velocity for the current vision system is calculated or otherwise determined (for example, by using a look-up table, or the like) based on the smear limit variable loaded at block 608 and the optimal exposure time determined at block 610 above. The calculation of the operational relative velocity involves generally four steps. First, a relative velocity is calculated based on the smear limit and the optimal exposure time. (Relative Velocity=Smear Limit/Optimal Exposure Time.) Second, the calculated relative velocity is compared with the maximum stage velocity of the current vision system loaded at block 604 above to determine which one has a lower value. Third, if the calculated relative velocity is lower, then it is set as the operational relative velocity for the current vision system. Fourth, on the other hand, if the maximum stage velocity is lower, the maximum stage velocity is set as the operational relative velocity for the current vision system.

At a block 614, optionally, the actual operational value of the smear limit variable is calculated from the operational relative velocity and the optimal exposure time determined for the current vision system, to see if it satisfies the maximum allowed value of the smear limit variable for the current image, loaded at block 608 above. (Actual Operational Smear Limit Value=Operational Relative Velocity×Optimal Exposure Time). If the calculated actual operational smear limit variable value deviates from the previously loaded allowable smear limit variable value by a predefined amount, an error may be reported to the user.

At a block 616, the image acquisition parameters associated with acquiring the current image, including the operational relative velocity, the optimal exposure time, and the chosen light power level, are recorded in memory as part of the workpiece image acquisition program instructions for the current image.

At a block 618, it is determined whether more image acquisitions are to be defined. If yes, returning to block 606, for the next image acquisition, blocks 608-616 are repeated to determine and store the image acquisition parameters for the next image.

If it is determined at block 618 that all image acquisitions have been defined, then at a block 620, operations are performed to travel along the motion path and execute the previously defined workpiece image acquisition instructions for the entire set of images, and to acquire and store or record the defined set of images of the workpiece to be inspected.

At a block 622, the acquired and stored images are recalled and analyzed or inspected. This operation is controlled by workpiece image analysis/inspection instructions, which are part of the overall part program for the workpiece. It will be appreciated that in some embodiments the storing of the images at block 620 and the recalling of the images at block 622 may be eliminated, or merged and indistinguishable. In addition, in some embodiments, analysis and/or inspection of the acquired images may begin before the acquisition of the entire set of images is complete. In other words, once the images have been acquired, they may be analyzed or inspected by a separate thread of operations without being first stored and then recalled, or, earlier-acquired images may be recalled and analyzed or inspected whenever computer processing time is available prior to completing acquisition of the entire set of images. These and other potential operation and/or processing sequences are described in greater detail in the previously incorporated '625 application.

At a block 624, the results of the image analysis/inspection are output or recorded. Block 624 completes the routine 600.

It should be noted that the routine 600 shown in FIG. 5 occurs during "run mode" of any vision system that subsequently uses a part program initially created according to this invention, for example, created according to the operations outlined with reference to FIG. 4. This "run mode" includes generally two types of instructions: the image acquisition parameter adaptation instructions (or machine-specific image acquisition optimization instructions) included in blocks 602-618, and the motion path traveling and analysis/inspection instructions included in blocks 620-624. By virtue of the image acquisition parameter adaptation instructions, the functional variables governing the image acquisition operations of the part program originally created on an initial vision system are used to automatically determine or adapt the image acquisition parameter instructions used with the current vision system, primarily based on a functional limit related to smear for one or more images of respective workpiece features to be inspected, in conjunction with a defined set operating characteristics or limitations for the current vision system. After the operations associated with the image acquisition parameter adaptation instructions, the image acquisition operations defined by the part program have been optimized, or nearly optimized, for the current vision system, so as to provide inspection images that support inspection results at the same level of accuracy achieved on the initial vision system, or better, while allowing the relative motion speed during image acquisition to be at the highest possible speed that is consistent with the required level of accuracy, in order to maximize the associated inspection throughput of the current vision system. The motion path traveling and analysis/inspection instructions then employ the previously defined optimized image acquisition operations/parameters to actually acquire and analyze/inspect the images.

It should be noted that the motion speed operable during the effective exposure time of an image, as determined by the strobe duration for example, determines the amount of motion smear (blur) in the corresponding inspection image. It is possible to define the values of the relative motion speed and exposure time "absolutely" in a part program (as opposed to defining these values relatively in terms of a functional limit related to smear according to this invention, as previously outlined herein). However, generally such a part program cannot be successfully executed on an assortment of different vision systems, unless the relative motion speed and exposure time are set according to the performance limits of the lowest-capability vision system(s) in the assortment. Thus, when such a part program is executed on any higher-capability vision system, the throughput of that higher-capability vision system will be limited at the same level as that of the lowest-capability vision system. This is in contrast to a part program generated according to various embodiments of the systems and methods according to the present invention, wherein both the operational relative speed and the optimal exposure time are defined in terms of a functional limit related to image smear, thus simultaneously providing for the acquisition of images that support a desired level of inspection and/or measurement accuracy, while also optimizing, or nearly optimizing, the inspection throughput of each specific vision system which uses the part program.

Figure 6:
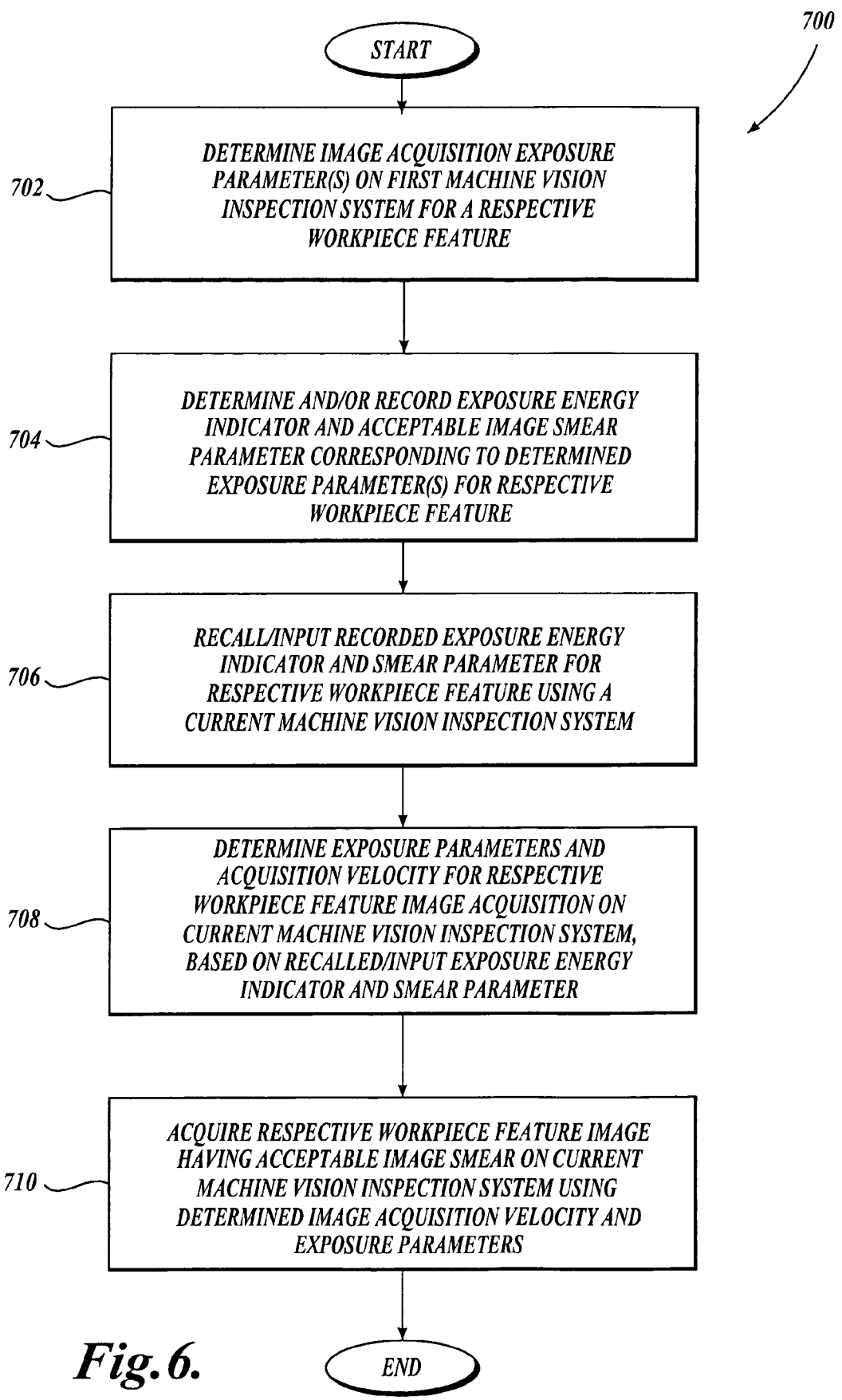
FIG. 6 is a flow diagram illustrating a generalized method of determining image acquisition exposure parameters for an acceptable image inspection image on a first machine vision system, recording a smear image parameter and an exposure energy indicator related to the image acquisition exposure parameters, and providing an image of the respective workpiece feature on a current machine vision system based on the recorded smear image parameter and the exposure energy indicator.

FIG. 6 is a flow diagram illustrative of one exemplary method or routine 700 for determining respective image acquisition exposure parameters on a first machine vision system that provide an acceptable workpiece image, recording an image smear parameter and an exposure energy indicator (or indicators) corresponding to the previously determined image acquisition exposure parameters in a set of workpiece inspection instructions, and using a machine vision inspection system to provide an image of the respective workpiece feature that has an acceptable image smear, based on the recorded smear image parameter and exposure energy indicator recorded in the workpiece inspection instructions. As will be more fully described below, the routine can automatically adapt to a given vision system. The automatic adaptation involves converting the recorded smear image parameter and exposure energy indicator determined on the first machine vision inspection system and recorded in the workpiece inspection instructions, to provide a combination of image exposure parameters and relative motion speed that is usable on a "current" machine vision inspection system to provide a properly exposed image having an acceptable amount of image smear.

At a block 702 of the routine 700, the essential operations use a first machine vision system to determine acceptable image acquisition exposure parameters for a respective workpiece feature. The exposure parameters generally include, or correspond to, a combination of an exposure time and a light source power setting that determines an overall exposure energy usable to produce a properly exposed image of the respective workpiece feature. These exposure parameters may be determined, for example, in a learn mode of operation of a machine vision inspection system. The particular combination of parameters that provides the overall exposure energy is not particularly critical, and need not be particularly machine-specific, since it is the total exposure energy (or a parameter indicative of, or corresponding to, the total exposure energy), not the particular combination, that is a relevant parameter used in the other operations of the routine 700 to determine the machine-specific combination of image acquisition exposure parameters to be used by a specific machine vision inspection system to provide an image of the respective workpiece feature.

As one example, for some machine vision inspection systems the light source power setting of a strobe light source may be set at a predetermined default power level, and an exposure time used with the default power level for exposure of the respective workpiece feature may be determined manually by a user who adjusts the exposure time (which may appear simply as an illumination level control to the user) until an acceptable image result is obtained. Alternatively, the exposure time for a default power level, or a combination of a variable power level and exposure time, may effectively be determined automatically with the aid of a semi-automatic or automatic lighting determination process similar to that disclosed in U.S. Pat. No. 6,627,863, to Wasserman, which is included herein by reference in its entirety.

At a block 704, the total exposure energy (or an exposure energy indicator that is a parameter indicative of, or corresponding to, the exposure energy) corresponding to the image acquisition exposure parameters determined in the operations of block 702 is recorded in a set of workpiece inspection instructions, for example a part program or the like. In addition, a smear parameter or functional variable indicative of a maximum level of image smear or an acceptable level of image smear in an inspection image of the respective feature is recorded in the instructions. In various embodiments, the smear parameter may be recorded during the operations that record the total exposure energy or a corresponding exposure energy indicator parameter. Alternatively, the smear parameter may be recorded by operations outside the operations of block 702, for example when a smear parameter is defined globally for a plurality of respective features. In various embodiments, the smear parameter may be determined and/or input manually by an operator, or semi-automatically, or automatically determined and input. The smear parameter may be a smear limit in terms of distance, or any other variable that is related to, or directly or indirectly indicative of an allowable amount of smear in a workpiece image that is used for inspection and measurement. For example, it may be defined as an imaging tolerance, such as a percentage of a dimension of the field of view of the camera, or a displacement in terms of camera pixels, or it may be defined as percentage of the dimensional tolerance of a feature to be inspected or measured in the image. Various methods of determining various types of limits that define the limits of acceptable image smear have been outlined previously.

At a block 706, the set of workpiece inspection instructions that include the recorded exposure energy indicator and smear parameter for the respective workpiece feature are input to a current machine vision inspection system, which may be, but is not required to be, a machine vision inspection system different from the first machine vision inspection system, and the recorded exposure energy indicator and smear parameter are recalled for use in subsequent operations of the current machine vision inspection system.

At a block 708, the current machine vision inspection system determines a combination of image acquisition exposure parameters and an image acquisition velocity for acquiring an inspection image of the respective workpiece feature while moving, based on the input and/or recalled exposure energy indicator(s) and smear parameter. Various principles and methods for determining a usable combination of image acquisition exposure parameters and image acquisition velocity have been previously described, thus they need not be described in detail here. However, as one example that is illustrative but not limiting, a first machine vision inspection system may comprise a set of respective calibrated values, each value calibrated to provide, or correspond to, a respective exposure energy arising from a combination of a relatively high light source power level and a relatively short exposure time. Such a value may be selected to provide a properly exposed image of the respective workpiece feature, and may also be used as the recorded exposure energy indicator at block 704. Furthermore, a current machine vision inspection system may comprise a set of respective calibrated values, calibrated to provide similar respective exposure energies in a manner similar to those of the first machine vision inspection system. In such a case, determining the image acquisition exposure parameters for the current machine at block 708 may comprise using the light source power level and exposure time that correspond to the calibrated value that is used as the recorded exposure energy indicator at block 704. The relative motion speed to be used in combination with these exposure parameters is then chosen based on the exposure time parameter for the current machine vision inspection system, so as to provide an image of the respective workpiece feature that has an accepted level of image smear. The principles for determining such a relative motion speed based on an image exposure time have been previously described herein.

At a block 710, the current machine vision inspection system uses the combination of image acquisition exposure parameters and relative motion speed to acquire an inspection image of the respective workpiece feature, such that the inspection image has an acceptable amount of image smear. Block 710 completes the routine 700 for the respective workpiece feature.

Of course, more generally, the operations of the blocks 702 and 704 may be repeated for a number of respective workpiece features and interspersed with a number of other machine control and image analysis and inspection instructions, for example in a learn mode of operation, in order to create a part program for a workpiece on a first machine visions inspection system. Then, the part program may be executed on a current machine vision inspection system, such that the operations of the blocks 706-710 may be repeated for a number of respective workpiece features and interspersed with a number of other machine control and image analysis and inspection instructions, for example in a run mode of operation, in order to inspect one or more workpieces according to the part program instructions.

It has previously been suggested herein that in various embodiments the light power level is set at the maximum possible level. However, it should be appreciated that this light power setting is exemplary only, and not limiting. In general, the light power level is set at any level that best enhances the image inspection operations to be performed on the image, and/or that provides an acceptable illumination source service life, and/or according to any other important operational consideration for a machine vision inspection system. In various exemplary embodiments, the light source that is used for strobing may include a Xenon flashlamp, a high intensity LED, such as one of the LEDs in the Luxeon™ product line, available from Lumileds Lighting, LLC, of San Jose, Calif., or any other suitable now-known or later-developed strobe light source. In one exemplary embodiment, the light source that is used for strobing may include a blue LED with a wavelength of approximately 470 nm. However, any wavelength within the sensing range of the camera can be used in various exemplary embodiments. Any of the previously described light sources 220-240 may be implemented using any of the previously described types of strobe lights.

While preferred and exemplary embodiments of the invention have been illustrated and described, it will be appreciated that various changes can be made therein according to the principles of this invention without departing from the spirit and scope of the invention.

The embodiments of the invention in which an exclusive property or privilege is claimed are defined as follows:

1. A method for programming a workpiece inspection program on a first precision machine vision inspection system, the precision machine vision inspection system comprising an image acquisition system comprising at least a camera; at least one light source; a workpiece stage; and a control system portion, wherein at least one of the workpiece stage and the camera is movable to provide relative motion with respect to each other, and wherein at least one of the camera and the light source defines a minimum effective exposure time of the precision machine vision inspection system, the method comprising:
   (a) determining acceptable image acquisition exposure parameters for an image of a respective workpiece feature;
   (b) recording at least one parameter indicative of an exposure energy corresponding to the determined image acquisition exposure parameters in the workpiece inspection program;
   (c) recording at least one parameter indicative of an acceptable image smear for the image of the respective workpiece feature in the workpiece inspection program; and
   (d) executing the workpiece inspection program on a current precision machine vision inspection system that is not the first precision machine vision inspection system and that has different specifications than the first precision machine vision inspection system, the current machine vision inspection system comprising an image acquisition system comprising at least a camera; at least one light source; a workpiece stage; and a control system portion that is not the control system portion of the first precision machine vision inspection system, the executing of the workpiece inspection program on the current machine vision inspection system comprising the substeps of:
      (i) receiving the at least one parameter indicative of an exposure energy recorded in the workpiece inspection program for the respective workpiece feature;
      (ii) receiving the at least one parameter indicative of an acceptable image smear recorded in the workpiece inspection program for the respective workpiece feature; and
      (iii) determining an operative combination of a light source power setting, an exposure time, and relative motion speed usable in conjunction with the exposure time on the current precision machine vision inspection system to provide an image smear not greater than the acceptable image smear.

2. The method of claim 1, wherein the at least one parameter indicative of an exposure energy defines a combination of a light source power setting and an exposure time.

3. The method of claim 2, wherein the first precision machine vision inspection system comprises a set of respective values usable to provide a respective exposure energy, determining the acceptable image acquisition exposure parameters comprises selecting one of the set of respective values, and recording at least one parameter indicative of an exposure energy corresponding to the determined image acquisition exposure parameters comprises recording the selected one of the set of respective values.

4. The method of claim 2, wherein the at least one parameter indicative of an acceptable image smear in the workpiece inspection program comprises one of (a) a relative motion speed usable in conjunction with the exposure time to provide an acceptable image smear and (b) an image smear parameter that defines an acceptable relative motion displacement during the exposure time.

5. The method of claim 2, wherein the exposure time is determined by one of (a) an effective light integration time duration of the camera, (b) an electronic shutter exposure duration of the camera, and (c) a strobe light time duration of the light source.

6. The method of claim 1, further comprising the sub-step of acquiring an image of the respective workpiece feature using the operative combination of light source power setting, exposure time, and relative motion speed.

7. A method for programming a workpiece inspection program on a first precision machine vision inspection system, the precision machine vision inspection system comprising an image acquisition system comprising at least a camera; at least one light source; a workpiece stage; and a control system portion, wherein at least one of the workpiece stage and the camera is movable to provide relative motion with respect to each other, and wherein at least one of the camera and the light source defines a minimum effective exposure time of the precision machine vision inspection system, the method comprising:

(a) determining acceptable image acquisition exposure parameters for an image of a respective workpiece feature;

(b) recording at least one parameter indicative of an exposure energy corresponding to the determined image acquisition exposure parameters in the workpiece inspection program, wherein the at least one parameter indicative of an exposure energy defines a combination of a light source power setting and an exposure time;

(c) recording at least one parameter indicative of an acceptable image smear for the image of the respective workpiece feature in the workpiece inspection program, wherein the at least one parameter indicative of an acceptable image smear in the workpiece inspection program comprises one of (c1) a relative motion speed usable in conjunction with the exposure time to provide an acceptable image smear and (c2) an image smear parameter that defines an acceptable relative motion displacement during the exposure time; and (d) executing the workpiece inspection program on a current precision machine vision inspection system that is one of (d1) the first precision machine vision inspection system and (d2) a precision machine vision inspection system that is not the first precision machine vision inspection system, comprising the sub-steps of:

(d-i) receiving the at least one parameter indicative of an exposure energy recorded in the workpiece inspection program for the respective workpiece feature;

(d-ii) receiving the at least one parameter indicative of an acceptable image smear recorded in the workpiece inspection program for the respective workpiece feature; and (d-iii) determining an operative combination of a light source power setting, an exposure time, and relative motion speed usable in conjunction with the exposure time on the current precision machine vision inspection system to provide an image smear not greater than the acceptable image smear;

wherein the first precision machine vision inspection system comprises a first set of respective values usable to control an image exposure and each respective value is usable to provide a corresponding calibrated exposure energy, the current precision machine vision inspection system comprises a current set of respective values usable to control an image exposure and each respective value is usable to provide a corresponding calibrated exposure energy, and similar respective values from the first and current sets of respective values on the first and current machines are usable to provide similar corresponding calibrated exposure energies, wherein:

the step of receiving the at least one parameter indicative of an exposure energy recorded in the workpiece inspection program comprises receiving one of the first set of respective values; and the step of determining an operative combination of a light source power setting, an exposure time, and relative motion speed comprises:

using one of the current set of respective values that is closest in value to the received one of the first set of respective values to determine the combination of a light source power setting and an exposure time in the current precision machine vision inspection system; and determining the relative motion speed in conjunction with the determined exposure time to provide an image smear not greater than the acceptable image smear.

8. The method of claim 7, wherein the first precision machine vision inspection system comprises a set of respective values usable to provide a respective exposure energy, determining the acceptable image acquisition exposure parameters comprises selecting one of the set of respective values, and recording at least one parameter indicative of an exposure energy corresponding to the determined image acquisition exposure parameters comprises recording the selected one of the set of respective values.

9. The method of claim 7, further comprising the sub-step of acquiring an image of the respective workpiece feature using the operative combination of light source power setting, exposure time, and relative motion speed.

10. The method of claim 7, wherein the exposure time is determined by one of (a) an effective light integration time duration of the camera, (b) an electronic shutter exposure duration of the camera, and (c) a strobe light time duration of the light source.

11. A method for programming and executing a workpiece part program such that it will execute efficiently on a first machine vision inspection system or on a second machine vision system having different specifications than the first machine vision inspection system, each machine vision inspection system comprising an image acquisition system comprising at least a camera; at least one light source; a workpiece stage; and a control system portion, wherein at least one of the workpiece stage and the camera is movable to provide relative motion with respect to each other, and wherein at least one of the camera and the light source defines a minimum effective exposure time of the precision machine vision inspection system, the method comprising:

(a) programming the workpiece part program on the first machine vision inspection system such that it will execute efficiently on the first machine vision inspection system or on a second machine vision system having different specifications than the first machine vision inspection system, comprising the sub-steps of:

(a-i) determining a value of a functional limit variable related to allowable image smear for an image of a respective workpiece feature and storing the value of the functional limit variable in the workpiece part program, for acquiring an image of the respective workpiece feature; and (a-ii) determining an operable exposure time at a defined light power level for acquiring an image of the respective workpiece feature and storing at least one parameter indicative of the product of the operable exposure time multiplied by the defined light power level in the workpiece part program, for acquiring an image of the respective workpiece feature; and (b) executing the workpiece part program on a current machine vision inspection system, comprising the sub-steps of:

(b-i) inputting from the current machine vision inspection system a maximum relative motion speed, a minimum effective exposure time and a maximum light power of the current machine vision inspection system;

(b-ii) inputting from the workpiece part program the value of the functional limit variable related to allowable image smear and the at least one parameter indicative of the product of the operable exposure time multiplied by the defined light power level, for acquiring an image of the respective workpiece feature;

(b-iii) determining an optimal exposure time for acquiring an image of the respective workpiece feature using the current machine vision inspection system, the optimal exposure time based on the at least one parameter indicative of the product of the operable exposure time multiplied by the defined light power level and a selected light power level that is equal to or less than the maximum light power of the current machine vision inspection system;

(b-iv) determining an operational relative velocity for acquiring the image of the respective workpiece feature using the current machine vision inspection system, the operational relative velocity based on the value of the functional limit variable and the optimal exposure time of the current machine vision inspection system for acquiring an image of the respective workpiece feature, wherein the operational relative velocity is equal to or less than the maximum relative motion speed of the current machine vision inspection system; and (b-v) acquiring an image of the respective workpiece feature using the determined operational relative velocity, the optimal exposure time, and the selected light power on the current machine vision inspection system such that the image of the respective workpiece feature has approximately the allowable amount of image smear corresponding to the value of the functional limit variable.

12. The method of claim 11, wherein the value of the functional limit variable comprises a smear limit.

13. The method of claim 11, wherein the optimal exposure time multiplied by the selected light level is approximately equal to the operable exposure time multiplied by the defined light power level.

14. The method of claim 11, wherein the current machine vision inspection system comprises a second machine vision inspection system wherein a specification for at least one of the maximum relative motion speed, the minimum effective exposure time, and the maximum light power of the second machine vision inspection system is different from the corresponding specification of the first precision machine vision inspection system.

15. The method of claim 11, wherein, in sub-step (b-iii), the maximum light power of the current machine vision inspection system is the selected light power level.

16. The method of claim 11, wherein, in sub-step (b-iii), determining an optimal exposure time for the second machine vision inspection system further comprises sub-sub-steps of:

(1) calculating a tentative exposure time based on the at least one parameter indicative of the product of the operable exposure time multiplied by the defined light power level and the selected light power level;

(2) comparing the calculated tentative exposure time with the minimum effective exposure time of the current system to determine which one has a longer value;

(3) if the calculated tentative exposure time is longer, setting the calculated tentative exposure time as the optimal exposure time; and (4) if the minimum effective exposure time is longer, setting the minimum effective exposure time as the optimal exposure time, and performing at least one of (a) re-calculating the selected light power level based on the at least one parameter indicative of the product of the exposure time multiplied by the defined light power level and the minimum effective exposure time and (b) re-calculating the operational relative velocity based on the value of the functional limit variable and the minimum effective exposure time.

17. The method of claim 11, wherein sub-step (b-iv) of calculating an operational relative velocity further comprises sub-sub-steps of:

(1) calculating a tentative relative velocity based on the value of the functional limit variable and the optimal exposure time;

(2) comparing the calculated tentative relative velocity with the maximum relative motion speed of the current system to determine which one has a lower value;

(3) if the calculated tentative relative velocity is lower, setting the calculated tentative relative velocity as the operational relative velocity; and (4) if the maximum relative motion speed of the current system is lower, setting the maximum relative motion speed as the operational relative velocity.

18. The method of claim 11, wherein steps (a) and (b) are repeated for each of a set of workpiece inspection images corresponding to respective workpiece features.

19. The method of claim 18, wherein a first value of the functional limit variable corresponds to a first respective workpiece feature, a second value of the functional limit variable corresponds to a second respective workpiece feature, and the first and second values of the function limit variable are different.

\* \* \* \* \*